US010787489B2

(12) United States Patent
Dexter

(10) Patent No.: US 10,787,489 B2
(45) Date of Patent: Sep. 29, 2020

(54) BIOCATALYST COMPRISING PHOTOAUTOTROPHIC ORGANISMS PRODUCING RECOMBINANT ENZYME FOR DEGRADATION OF HARMFUL ALGAL BLOOM TOXINS

(71) Applicant: Jason Dexter, Olean, NY (US)

(72) Inventor: Jason Dexter, Olean, NY (US)

( * ) Notice: Subject to any disclaimer, the term of this patent is extended or adjusted under 35 U.S.C. 154(b) by 0 days.

(21) Appl. No.: 16/307,783

(22) PCT Filed: Jul. 20, 2017

(86) PCT No.: PCT/US2017/043061
§ 371 (c)(1),
(2) Date: Dec. 6, 2018

(87) PCT Pub. No.: WO2018/017828
PCT Pub. Date: Jan. 25, 2018

(65) Prior Publication Data

US 2019/0263871 A1 Aug. 29, 2019

(51) Int. Cl.

| | |
|---|---|
| ***C07K 14/195*** | (2006.01) |
| ***C12N 1/12*** | (2006.01) |
| ***C12N 1/20*** | (2006.01) |
| ***C12N 9/50*** | (2006.01) |
| ***C12N 15/03*** | (2006.01) |
| ***C12N 15/52*** | (2006.01) |
| ***C12N 15/82*** | (2006.01) |
| ***C12N 9/52*** | (2006.01) |

(52) U.S. Cl.
CPC .............. *C07K 14/195* (2013.01); *C12N 1/12* (2013.01); *C12N 1/20* (2013.01); *C12N 9/50* (2013.01); *C12N 9/52* (2013.01); *C12N 15/03* (2013.01); *C12N 15/52* (2013.01); *C12N 15/82* (2013.01)

(58) Field of Classification Search
None
See application file for complete search history.

(56) References Cited

U.S. PATENT DOCUMENTS

| | | | |
|---|---|---|---|
| 7,425,267 | B2 | 9/2008 | Sumino |
| 8,192,970 | B2 | 6/2012 | Sumino |
| 2006/0096915 | A1 | 5/2006 | Sumino |

OTHER PUBLICATIONS

Wijffels R et al. Potential of industrial biotechnology with cyanobacteria and eukaryotic microalgae. 2013. Current Opinion in Biotechnology. 24:405-413. (Year: 2013).*

Prather KLJ et al. De novo biosynthetic pathways: rational design of microbial chemical factories. 2008. Current Opinion in Biotechnology. 19:468-474 (Year: 2008).*

Kizer L et al. Application of Functional Genomics to Pathway Optimization for Increased Isoprenoid Production. 2008. Applied and Environmental Microbiology. p. 3229-3241 (Year: 2008).*

Guerrero F et al. Ethylene synthesis and Regulated Expression of Recombinant Protein in *Synechocystis* sp. PCC 6803. PLOS One. 2012. vol. 7, issue 11. (Year: 2012).*

Dexter et al. 'Heterologous expression of mlrA in a photoautotrophic host—Engineering cyanobacteria to degrade microcystins'. Environmental Pollution. Available online Feb. 15, 2018. pp. 926-935. vol. 237. Elsevier. Amsterdam, The Netherlands.

Bourne et al. 'Enzymatic pathway for the bacterial degradation of the cyanobacterial cyclic peptide toxin microcystin LR'. Applied and Environmental Microbiology. Nov. 1996. pp. 4086-4094. vol. 62, Issue 11. Elsevier. Amsterdam, The Netherlands.

Bourne et al. 'Characterisation of a gene cluster involved in bacterial degradation of the cyanobacterial toxin microcystin LR'. Environmental Toxicology. Nov. 15, 2001. pp. 523-534. vol. 16, Issue 6. John Wiley & Sons, Inc. Hoboken, US.

Yan et al. 'Cloning and expression of the first gene for biodegrading microcystin LR by *Sphingopyxis* sp. USTB-05'. Journal of Environmental Sciences. Available online Oct. 8, 2012. pp. 1816-1822. vol. 24, Issue 10. Elsevier. Amsterdam, The Netherlands. Posted Sep. 1, 2010 in Nature Proceedings (Attached version).

Yan et al. 'Characterization of the first step involved in enzymatic pathway for microcystin-RR biodegraded by *Sphingopyxis* sp. USTB-05'. Chemosphere. Available online Dec. 15, 2011. pp. 12-18. vol. 87, Issue 1. Elsevier. Amsterdam, The Netherlands.

Dziga et al. 'Heterologous expression and characterisation of microcystinase'. Toxicon. Available online Feb. 1, 2012. pp. 578-586. vol. 59, Issue 5. Elsevier. Amsterdam, The Netherlands.

Dziga et al. 'Microbial Degradation of Microcystins'. Chemical Research in Toxicology. Apr. 26, 2013. pp. 841-852. vol. 26, Issue 6. ACS Publications. Washington DC, US.

Dziga et al. 'Bioreactor Study Employing Bacteria with Enhanced Activity toward Cyanobacterial Toxins Microcystins'. Toxins. Aug. 13, 2014. pp. 2379-2392. vol. 6, No. 8. MDPI. Basel, Switzerland.

(Continued)

*Primary Examiner* — Paul J Holland

(57) ABSTRACT

The invention comprises a photoautotrophic organism, generally having simpler nutritional requirements than heterotrophic organisms, utilized as a chassis for the heterologous expression and function of enzymes, or derivatives of said enzymes, that show activity toward the degradation/detoxification of toxins known to be associated with and specific to harmful algal blooms. As an example, a cyanobacterial strain (*Synechocystis* sp. PCC 6803) modified to express *Sphingomonas* sp. USTB-05 MlrA enzyme functionality, showing the capability of degrading microcystins (results shown here) and nodularins, is presented. Under modelled natural conditions, results indicate that heterologous enzymatic activity against microcystin-LR is more stable over time when utilizing a photoautotrophic chassis in comparison to use of a heterotrophic bacterial strain. In addition, both the viability and cell density of the photoautotrophic host is maintained for a significantly longer period of time, compared to a heterotrophic host.

6 Claims, 2 Drawing Sheets

Figure 1:
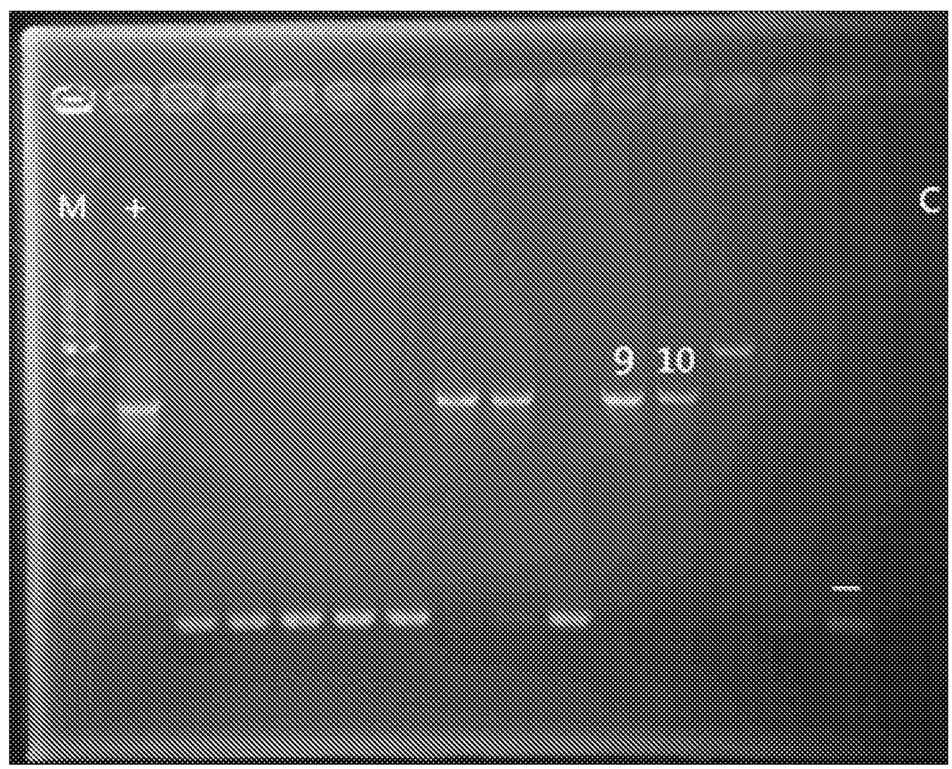

Specification includes a Sequence Listing.

(56) References Cited

OTHER PUBLICATIONS

Dziga et al. 'Characterization of Enzymatic Activity of MlrB and MlrC Proteins Involved in Bacterial Degradation of Cyanotoxins Microcystins'. Toxins. Mar. 16, 2016. pp. 1-13. vol. 8, Issue 76. MDPI. Basel, Switzerland.

Kuritz and Wolk. 'Use of filamentous cyanobacteria for biodegradation of organic pollutants'. Applied and Environmental Microbiology. Jan. 1, 1995. pp. 234-238. vol. 61, Issue 1. American Society for Microbiology. Washington DC, US.

Kuritz. 'Cyanobacteria as agents for the control of pollution by pesticides and chlorinated organic compounds'. Journal of Applied Microbiology. Dec. 1998. pp. 186S-192S. vol. 85, Issue S1. John Wiley & Sons, Inc. Hoboken, US.

Idi et al. 'Photosynthetic bacteria: an eco-friendly and cheap tool for bioremediation'. Reviews in Environmental Science and Bio/Technology. First Online: Oct. 18, 2014. pp. 271-285. vol. 14, Issue 2. Springer Nature. New York City, US.

Li et al. 'Current research scenario for microcystins biodegradation—A review on fundamental knowledge, application prospects and challenges'. Science of the Total Environment. Apr. 11, 2017. pp. 615-632. vol. 595. Elsevier. Amsterdam, The Netherlands.

Wang et al. 'Heterologous expression of mlrA gene originated from *Novosphingobium* sp. THN1 to degrade microcystin-RR and identify the first step involved in degradation pathway'. Chemosphere. Available online May 17, 2017. pp. 159-167. vol. 184. Elsevier. Amsterdam, The Netherlands.

Pflugmacher et al. 'Uptake, effects, and metabolism of cyanobacterial toxins in the emergent reed plant Phragmites australis (cav.) trin. ex steud.'. Environmental Toxicology and Chemistry. Apr. 2001. pp. 846-852. vol. 20, Issue 4. John Wiley & Sons, Inc. Hoboken, US.

Pflugmacher et al. 'Physiological responses of Cladophora glomerata to cyanotoxins: a potential new phytoremediation species for the Green Liver Systems'. Toxicological and Environmental Chemistry. Dec. 16, 2015. pp. 241-259. vol. 98, Issue 2. Elsevier. Amsterdam, The Netherlands.

Nimptsch et al. 'Cyanobacterial toxin elimination via bioaccumulation of MC-LR in aquatic macrophytes: an application of the "Green Liver Concept"'. Environmental Science & Technology. Oct. 23, 2008. pp. 8552-8557. vol. 42, Issue 22. ACS Publications. Washington DC, US.

Babica et al. 'Removal of microcystins by phototrophic biofilms. A microcosm study'. Environmental Science and Pollution Research. Jan. 2005. pp. 369-374. vol. 12, Issue 6. Springer Nature. New York City, US.

Edwards and Lawton. 'Bioremediation of cyanotoxins'. Advances in Applied Microbiology. Available online Feb. 24, 2009. pp. 109-129. vol. 67. Elsevier. Amsterdam, The Netherlands.

Ho et al. 'Biological treatment options for cyanobacteria metabolite removal—A review'. Water Research. Available online Nov. 15, 2011. pp. 1536-1548. vol. 46, Issue 5. Elsevier. Amsterdam, The Netherlands.

Bartsch et al. 'Photosynthetic production of enantioselective biocatalysts'. Microbial Cell Factories. Apr. 15, 2015. vol. 14, Issue 53. BMC, part of Springer Nature. New York City, US.

Manage et al. 'Bacterial Degradation of Microcystin'. Interdisciplinary Studies on Environmental Chemistry—Biological Responses to Contaminants. Jan. 2010. pp. 97-104. TERRAPUB. Tokyo, Japan.

Pflugmacher et al. 'Green Liver Systems® for Water Purification: Using the Phytoremediation Potential of Aquatic Macrophytes for the Removal of Different Cyanobacterial Toxins from Water'. American Journal of Plant Sciences. Jun. 29, 2015. pp. 1607-1618. vol. 6, Issue 9. Scientific Research Publishing (SCIRP). Wuhan, China.

Dziga et al. 'Genetically Engineered Bacteria Immobilized in Alginate as an Option of Cyanotoxins Removal'. International Journal of Environmental Science and Development. Jan. 2013. pp. 360-364. vol. 4, Issue 4.

Shimizu et al. 'Enzymatic pathway for biodegrading microcystin LR in *Sphingopyxis* sp. C-1'. Journal of Bioscience and Bioengineering. Aug. 9, 2012. pp. 630-634. vol. 114, Issue 6. Elsevier. Amsterdam, The Netherlands.

Li et al. 'Simultaneous Microcystis Algicidal and Microcystin Degrading Capability by a Single Acinetobacter Bacterial Strain'. Environmental Science and Technology. Oct. 6, 2016. pp. 11903-11911. vol. 50, Issue 21. ACS Publications. Washington DC, US.

Dziga et al. 'Verification of the role of MlrC in microcystin biodegradation by studies using a heterologously expressed enzyme'. Chemical Research in Toxicology. May 16, 2012. pp. 1192-1194. vol. 25, Issue 6. ACS Publications. Washington DC, US.

Górak and Żymanczyk-Duda. 'Application of cyanobacteria for chiral phosphonate synthesis'. Green Chemistry. Jul. 14, 2015. pp. 4570-4578. vol. 17, Issue 9. Royal Society of Chemistry. Washington DC, US.

(Website) http://2016.igem.org/Team:Aalto-Helsinki/Description Describes the heterologous expression of MlrA in yeast.

(Website) http://2014.igem.org/Team:Peking/Degradation Describes the heterologous expression of MlrA in *E. coli* BL21 (DE3).

(Poster Presentation) Tlalka et al. 'Modification of Synechocystis PCC 6803mlrAsec+ construct by introduction of trc promoter'. Portuguese Society of Genetics, Annual Meeting, Jun. 14-15, 2018, Porto, Portugal. Disclosed after both priority and international filing dates of the current application, thus not affecting the patentability of the current application.

(Closed lab group discussion [Not advertised, not posted, no materials distributed]—slides used for discussion attached) Dexter. 'Goldilocks Economics Within Emerging Algal Biotechnology' Oct. 31, 2016. Beijing University of Chemical Technology. Beijing, China.

* cited by examiner

BIOCATALYST COMPRISING PHOTOAUTOTROPHIC ORGANISMS PRODUCING RECOMBINANT ENZYME FOR DEGRADATION OF HARMFUL ALGAL BLOOM TOXINS

CROSS-REFERENCE TO RELATED APPLICATIONS

This application claims the benefit of U.S. Provisional Application No. 62/365,301, filed Jul. 21, 2016.

STATEMENT REGARDING FEDERALLY SPONSORED RESEARCH

Not applicable.

FIELD OF THE INVENTION

Water treatment, specifically: organisms and methodologies associated with biologically based degradation of toxins associated with and specific to harmful algal blooms. Plant/algae/cyanobacterial biotechnologies utilizing heterologous gene expression.

BACKGROUND OF THE INVENTION

Harmful algal blooms, the rapid increase and resulting population of naturally present toxin-producing phytoplankton, are a global environmental concern, with increasing eutrophication due to agricultural runoff and increasing temperatures poised to amplify the problem with expanding commercial agriculture and climate change. Different methods are available for the treatment of waters contaminated with harmful algal bloom toxins based on: adsorption of toxin to various adsorbents (activated charcoal, for example), oxidation of toxins via chemical application (chlorination, ozonation, permanganate, peroxides), photocatalytic degradation via light exposure in the presence of certain chemical catalysts, and biodegradation of toxins via organisms (typically water-borne bacteria) having this specific capacity. Biodegradation is considered to be a primary natural process in the detoxification of contaminated waters. Naturally developing bacterial ecologies in aqueous systems, utilizing naturally occurring organisms with toxin degrading capacity, can show reduced rate of toxin degradation compared to organisms heterologously expressing a toxin degrading enzymatic pathway, given the capacity to generate relatively higher quantities of the enzyme/enzymatic pathway during heterologous expression. Yet, despite the ability to greatly increase the enzymatic production, said systems for heterologous expression are, similar to the native enzyme-containing organisms, utilizing heterotrophic organisms, thus by necessity require a fixed carbon source for growth along with potentially other complex nutrients. Utilization of a photoautotrophic chassis rather than a heterotrophic chassis can allow for biosynthesis of the physical components of the toxin degrading enzymatic pathway via a chassis that has reduced substrate requirements for growth. This may allow for more economical production of the physical components (enzymes) responsible for toxin biodegradation, allowing for new, lower-input, lower-cost biodegradation-based methodologies. Current chemical or adsorption-based detoxification processes may prove to be more capital intensive than utilization of a regenerative biologically-based catalyst for detoxification, especially considering the biologically-based catalyst is produced in a chassis that can sustain prolonged exposure to and/or growth in the surface water matrix.

Biological degradation of microcystins has been shown to be the primary natural process for the remediation of contaminated waters, with the ecological presence of mlr genes associated with greatly accelerated microcystin degradation compared to microbial consortia utilizing mlr-independent degradation pathways. MlrA is a metalloprotease acting specifically at the peptide bond between Adda- and the fourth position amino acid, catalyzing the initiating reaction in the mlr-dependent degradation pathway, linearizing the microcystin heptapeptide ring structure, and resulting in a 160-fold decrease in toxicity (in some reports, 2100-fold decrease in toxicity), essentially rendering a non-toxic product.

DETAILED DESCRIPTION

The present invention comprises a photoautotrophic organism modified to express a heterologous enzymatic pathway that functions to degrade toxins associated with and specific to harmful algal blooms.

In some embodiments of the invention, a single toxin is targeted for degradation by said enzymatic pathway. In other embodiments of the invention, an entire class of related toxins is targeted for degradation by said enzymatic pathway. Furthermore, in some embodiments of the invention multiple toxin classes are targeted for degradation by a single enzymatic pathway. Also, in some embodiments of the invention multiple toxin classes are targeted for degradation by multiple enzymatic pathways, with each pathway functioning to degrade at least one member of one or more of the target toxin classes. In addition, in some embodiments of the invention multiple enzymatic pathways are heterologously expressed, with all pathways targeting a single toxin or class of toxins.

In any of the above cases, the toxins that may be targeted for degradation are those that are associated with and specific to harmful algal blooms. The following list provides some examples of representative harmful algal bloom toxins and toxin classes, but it does not offer every known toxin or class of toxin.

(1) Microcystins. Microcystins are a class of toxins that are the most widely distributed and most abundant toxins associated with freshwater harmful algal blooms. There are over 80 unique chemical structures identified as microcystins, although all members of the class of microcystins are not equally represented, both in terms of total environmental biosynthesis and in toxic effect. Microcystin-LR is the most toxic member of the class of microcystins and is also the most commonly observed microcystin. Other microcystins include: microcystin-RR, microcystin-YR, microcystin-LA, microcystin-LY, microcystin-LW, microcystin-LF. Chemically, microcystins comprise cyclic heptapeptides produced through nonribosomal peptide synthesis, with the suffixes (-LR, -RR, -YR, -LA, etc.) representing the amino acids at two fundamental variable positions in the heptapeptide.

(2) Nodularins. Nodularins are a class of toxins chemically related to microcystins in that they are produced via nonribosomal peptide synthesis, and comprise a group of approximately 10 known unique chemical structures that are cyclic pentapeptides, with nodularin-R being the most widely observed. Nodularins are also globally distributed, being produced by the cyanobacteria *Nodularia spumigena.*

(3) Cylindrospermopsin, a specific toxin.

(4) Anatoxin-a, a specific toxin.

(5) Dinotoxins, Saxitoxins, Gonyautoxins and Yessotoxins. Classes of toxins. As a preferred embodiment and as reduced to practice, an example is provided of a photoautotrophic organism modified to express a single heterologous enzymatic pathway that functions to degrade at least one member from multiple toxin classes, those toxin classes being microcystins and nodularins.

In some embodiments of the invention, the enzymatic pathway utilized for toxin degradation comprises a single enzyme. In other embodiments of the invention, the enzymatic pathway utilized for toxin degradation comprises multiple no enzymes. As a preferred embodiment and as reduced to practice, an example is provided of a photoautotrophic organism expressing a single heterologous enzymatic pathway comprising a single enzyme that functions to degrade at least one member of the group of toxins microcystins and nodularins.

In some preferred embodiments of the invention, at least one of the enzymes employed in the heterologously expressed enzymatic pathway is a member of the type II CAAX proteases and bacteriocin-processing metalloproteases family, and said enzyme demonstrates enzymatic activity towards at least one member of the group of toxins microcystins and nodularins.

In some preferred embodiments of the invention, the amino acid sequence of at least one of the enzymes employed in the heterologously expressed enzymatic pathway is homologous with at least one member of the enzymes functionally annotated as 'microcystin degrading enzyme', 'microcystinase', and 'MlrA' (with MlrA referencing the microcystin degrading enzyme) in the NCBI publicly available protein database, and said enzyme demonstrates enzymatic activity towards at least one member of the group of toxins microcystins and nodularins.

In some preferred embodiments, in addition to the above-mentioned homologies, the enzyme amino acid sequence contains a HXXHXE amino acid sequence element (SEQ ID No: 6) (where H is histidine, X is any amino acid, and E is glutamic acid), a site of metal ion chelation at the enzyme active site, as one means of enabling the activity of the MlrA enzyme. In some preferred embodiments, the amino acid sequence HAIHNE (SEQ ID No: 7) constitutes this HXXHXE element. In some preferred embodiments of the invention the amino acid sequence of at least one of the enzymes employed in the heterologously expressed enzymatic pathway is identical to one member of the enzymes functionally annotated as 'microcystin degrading enzyme', 'microcystinase', and 'MlrA' (with MlrA referencing the microcystin degrading enzyme) in the NCBI publicly available protein database, and said enzyme demonstrates enzymatic activity towards at least one member of the group of toxins microcystins and nodularins. In some examples of such preferred embodiments of the invention, the enzyme is selected from the following list:

(1) microcystin degrading enzyme MlrA [*Sphingopyxis* sp. C-1]. SEQ ID No: 8.
(2) microcystin degrading enzyme MlrA, partial [*Sphingopyxis* sp.]. SEQ ID No: 9.
(3) microcystin degrading enzyme MlrA, partial [*Sphingopyxis* sp. MB-E]. SEQ ID No: 10.
(4) MlrA, partial [*Sphingomonas* sp. ACM-3962]. SEQ ID No: 11.
(5) MlrA [*Novosphingobium* sp. THN1]. SEQ ID No: 12.
(6) MlrA, partial [*Sphingomonas* sp. USTB-05]. SEQ ID No: 13.
(7) MlrA [*Rhizobium* sp. TH]. SEQ ID No: 14.

The above list is not a complete list of all enzymes that fit the requirement; rather the enzymes listed above serve as representative examples of enzymes that may be utilized for heterologous expression within the scope of the present invention.

As a preferred embodiment and as reduced to practice, an example is provided of a photoautotrophic organism modified to express a heterologous enzymatic pathway comprising an enzyme that is a member of the type II CAAX proteases and bacteriocin-processing metalloproteases family, is homologous to at least one member of the enzymes functionally annotated as 'microcystin degrading enzyme', 'microcystinase', and 'MlrA' (with MlrA referencing the microcystin degrading enzyme) in the NCBI publicly available protein database, said enzyme amino acid sequence contains a HXXHXE amino acid sequence element allowing said enzyme to function to degrade at least one member of the toxins of the group of microcystins and nodularins.

As a preferred embodiment and as reduced to practice, an example is provided of a photoautotrophic organism modified to express a single heterologous enzymatic pathway comprising a single enzyme: *Sphingomonas* sp. USTB-05 MlrA that functions to degrade at least one member of the toxins of the group of microcystins and nodularins.

The criteria for the enzyme listed above: "... is a member of the type II CAAX proteases and bacteriocin-processing metalloproteases family, and said enzyme demonstrates enzymatic activity towards at least one member of the group of toxins microcystins and nodularins." and "... is homologous with at least one member of the enzymes functionally annotated as 'microcystin degrading enzyme', 'microcystinase' and 'MlrA' in the NCBI publicly available protein database, and said enzyme demonstrates enzymatic activity towards at least one member of the group of toxins microcystins and nodularins." can be verified for said enzyme through standard practices known in the art. For example, primers and PCR assay conditions have been previously described for probing complex environmental samples for the presence of both (independently) mlrA genes and genes belonging to the type II CAAX proteases and bacteriocin-processing metalloproteases family. Use of similar primers or degenerative primers designed for amplification of at least the whole gene sequence of said enzyme which can then be determined via sequencing and comparison of the sequencing data to previously known complete MlrA (336 amino acids) and type II CAAX proteases and bacteriocin-processing metalloproteases in publicly available databases. Furthermore, verification of enzymatic activity towards microcystins and/or nodularins can be performed via microbial culture of the natural gene host, assaying for microcystin and/or nodularin degradation over time, when supplied with a known concentration of microcystin and/or nodularin, respectively.

In some embodiments of the invention the native gene sequence coding for the enzyme or enzymes comprising the degradation pathway is utilized, while in other embodiments codon optimization is performed on the genetic sequence coding for one or more of the enzymes comprising the degradation pathway. The codon optimization algorithm may or may not be specific to the photoautotrophic organism modified to express the enzymatic pathway. In the below examples, the gene encoding *Sphingomonas* sp. USTB-05 MlrA has been codon optimized with respect to the chosen photoautotrophic organism (*Synechocystis* sp. PCC 6803). As mentioned above, in some embodiments of the invention the enzymatic pathway utilized for toxin degradation comprises multiple enzymes, as a preferred embodiment, coexpression with any of the above described enzymes with any subset of enzymes showing homology with at least one member of the group of enzymes functionally annotated as (1) MlrB, (2) MlrC, (3) MlrD, (4) MlrE and (5) MlrF (from the mlr degradation pathway) in the NCBI publicly available protein database, and said enzyme(s) demonstrates enzymatic activity towards at least one member of the group consisting of microcystins, nodularins, and the reaction products arising from said toxin degradation resulting from other enzymes constituting the heterologous enzymatic pathway. In some embodiments, these above enzymes (MlrB-MlrF) may be co-expressed with MlrA, to allow for further degradation of the linearized microcystin (resultant from MlrA). As a preferred embodiment, MlrB and/or MlrC are co-expressed with MlrA for this purpose. In some embodiments, the amino acid pool resultant from this process (further degradation of the linearized microcystin) might be utilized as a positive selective pressure in either a photoautotrophic amino acid auxotroph (arginine auxotroph for example) or photoautotrophic isolate evolved for growth-coupled utilization of novel metabolic resources (such as arginine resulting from the degradation of microcystin-LR, for example). In such a strain, the positive selective pressure of rapid microcystin degradation might allow for evolution of such a trait via gradual substitution of microcystin-LR with the primary nitrogen source over extended culturing.

In some embodiments of the invention the amino acid sequences of one or more of the enzymes of the heterologous enzymatic pathway are modified by the addition to the N-terminus and/or C-terminus of additional amino acids. These additional amino acids may or may not fundamentally alter the reaction(s) catalyzed by the enzyme, and may or may not alter the utility of the enzyme via a number of mechanisms, including but not limited to: (1) enhancement of enzyme activity, (2) alteration of enzyme specificity, (3) localization of the enzyme to a particular cellular structure, (4) modulation of RNA expression rate (transcription), (5) modulation of RNA transcript stability (post-transcription), (6) facilitating the folding trajectory of the polypeptide comprising the enzyme, and (7) enhancing the stability of the enzyme.

As a preferred embodiment and as reduced to practice, an example is provided of a photoautotrophic organism modified to express a single heterologous enzymatic pathway comprising a single enzyme: *Sphingomonas* sp. USTB-05 MlrA with a 23 amino acid N-terminal peptide tag consisting of: (from N-terminal of said tag) the first 21 amino acids of the *Synechocystis* sp. PCC 6803 PilA gene (sll1694) followed by a Methionine followed by a Glycine, that functions to degrade at least one member of the toxins of the group of microcystins and nodularins.

Although not a complete list, additional preferred examples of N-terminal and/or C-terminal modifications where the primary function of the enzyme is preserved include:

(1) His-tag (hexahistadine, or other related his tag) addition,
(2) FLAG tag addition,
(3) Generation of glutathione S-transferase (GST) fusion protein,
(4) Generation of maltose-binding protein (MBP) fusion protein,
(5) Cellulose binding module (CBM) addition, and other affinity tag additions,
(6) *Synechocystis* sp. PCC 6803 phycocyanan ß-subunit (CpcB) fusion protein, (shown to increase enzyme titers in *Synechocystis* sp. PCC 6803),
(7) Insertion of enzyme coding sequence into the coding sequences of external regions of outer membrane proteins (such as cyanobacterial porin SomA, comparable to techniques shown with *Synechococcus elongatus* PCC 7942 SomA), allowing the enzyme to be localized to the exterior surface of the bacterial outer membrane, giving greater access of the target enzyme functional group to the external environment, facilitating mass transfer of the toxin to the enzyme functional group,
(8) Addition of an Encapsulation Peptide (EP)—a peptide that mediates interactions with other proteins involved in the assembly of bacterial microcompartments, allowing for the localization of the enzyme to the bacterial microcompartment, this may reduce toxicity associated with protein overexpression, it also may increase the stability of the enzyme and/or allow for increased activity associated with increased localized enzyme density.
(9) In some embodiments of the invention, multiple modifications are made to the N-terminal and/or C-terminal, including but not limited to any combinations of the above modifications.

In preferred embodiments of the invention, the genes coding for the enzymes of the enzymatic pathway are transcribed under the action of a promoter. In some embodiments, each gene in the enzymatic pathway is transcribed by a unique operably linked promoter, in other embodiments the genes are transcriptionally linked in an operon under the control of a single promoter. In some embodiments, promoters native to the photoautotrophic organism are utilized for gene expression, in other embodiments, promoters not native to the photoautotrophic organism are utilized for gene expression (such as the trc promoter, as a preferred example), still in other embodiments both native and non-native promoters are utilized in the final genetic construct that functions to express the enzymatic pathway. As a preferred embodiment, the enzymatic pathway comprising a single enzyme: *Sphingomonas* sp. USTB-05 MlrA with a 23 amino acid N-terminal peptide tag consisting of: (from N-terminal of said tag) the first 21 amino acids of the *Synechocystis* sp. PCC 6803 PilA gene (sll1694) followed by a Methionine followed by a Glycine, is expressed under the control of the *Synechocystis* sp. PCC 6803 cpcB560 promoter. As a preferred embodiment, and reduced to practice the cpcB560 promoter above is modified via the substitution of the final 3' base of this promoter from A to C. As another preferred embodiment and also reduced to practice, the final 3' base of the cpcB560 promoter is deleted from the genetic construct, this promoter was utilized in an attempt to express codon optimized *Sphingomonas* sp. USTB-05 MlrA without the 23 amino acid N-terminal peptide tag described above. Regarding the genetic cassette responsible for heterologous expression of the enzymatic pathway, in some embodiments said genetic cassette is incorporated into an extra-chromosomal plasmid that is stably maintained within the photoautotrophic organism. In some embodiments, this extra-chromosomal plasmid is a plasmid native to the photoautotrophic organism, in other preferred embodiments this extra-chromosomal plasmid is a non-native plasmid (for example RSF1010-derived plasmid transformation of cyanobacteria). Insertion of the enzyme expression cassette into such broad host-range vectors (RSF1010) allows for rapid comparisons of the enzyme activity and expression system functionality across a wide range of cyanobacterial isolates after respective transformation. When considering eukaryotic photoautotrophic organisms, the genetic cassette responsible for heterologous expression of the enzymatic pathway may be targeted for integration into either the nuclear, chloroplast, or mitochondrial genomes. In some embodiments, said genetic cassette is targeted for insertion into the photoautotrophic organism's chromosome(s). As a preferred embodiment, and as reduced to practice, the genetic cassette responsible for heterologous expression of the enzymatic pathway is targeted for integration into the chromosome of photoautotrophic organism *Synechocystis* sp. PCC 6803. As a preferred embodiment, and as reduced to practice, the genetic cassette responsible for heterologous expression of the enzymatic pathway is targeted for integration into the chromosome, and the integrating event occurs via double homologous recombination between a plasmid containing the genetic cassette responsible for heterologous expression of the enzymatic pathway and the photoautotrophic organism's chromosome. As a preferred embodiment, and as reduced to practice said genetic cassette is targeted for double homologous recombination at the slr0271 genomic locus of *Synechocystis* sp. PCC 6803. In some embodiments of the invention, one or multiple selectable genetic markers are additionally incorporated into said genetic cassette to facilitate isolation of the transformed cell line showing complete segregation for the desired genetic modification. As a preferred embodiment, and as reduced to practice, the aphAI kanamycin resistance gene is incorporated into the above said genetic cassette to act as a selectable genetic marker.

In some embodiments of the invention, the photoautotrophic organism utilized is a member of the eukaryotic group of organisms known as algae. In other embodiments of the invention the photoautotrophic organism utilized is a member of the phylum Cyanobacteria.

In some embodiments of the invention, the photoautotrophic organism utilized for expression of the heterologous enzymatic pathway is from the following list: *Cyanidioschyzon merolae, Thalassiosira pseudonana, Chlamydomonas reinhardtii, Volvox carteri, Ostreococcus tauri, Synechocystis* sp. WHSyn, *Synechococcus elongatus* UTEX 2973, "*Nostoc azollae*" 0708, *Acaryochloris marina* MBIC11017, *Anabaena cylindrica* PCC 7122, *Anabaena* sp. 90, *Anabaena* sp. wa102, *Anabaena variabilis ATCC* 29413, *Calothrix* sp. 336/3, *Calothrix* sp. PCC 6303, *Calothrix* sp. PCC 7507, *Chlorobium tepidum* TLS, *Chroococcidiopsis thermalis* PCC 7203, *Crinalium epipsammum* PCC 9333, *Cyanobacterium aponinum* PCC 10605, *Cyanobacterium stanieri* PCC 7202, *Cyanobium gracile* PCC 6307, *Cyanothece* sp. ATCC 51142, *Cyanothece* sp. PCC 7424, *Cyanothece* sp. PCC 7425, *Cyanothece* sp. PCC 7822, *Cyanothece* sp. PCC 8801, *Cyanothece* sp. PCC 8802, *Dactylococcopsis salina* PCC 8305, *Geitlerinema* sp. PCC 7407, *Gloeobacter kilaueensis* JS1, *Gloeobacter violaceus* PCC 7421, *Gloeocapsa* sp. PCC 7428, *Halothece* sp. PCC 7418, *Leptolyngbya* sp. PCC 7376, *Microcoleus* sp. PCC 7113, *Nostoc punctiforme* PCC 73102, *Nostoc* sp. PCC 7107, *Nostoc* sp. PCC 7120, *Nostoc* sp. PCC 7524, *Oscillatoria acuminate* PCC 6304, *Oscillatoria nigro-viridis* PCC 7112, *Pleurocapsa* sp. PCC 7327, *Prochlorococcus marinus* str. AS9601, *Prochlorococcus marinus* str. MIT 9215, *Prochlorococcus marinus* str. MIT 9301, *Pseudanabaena* sp. PCC 7367, *Rivularia* sp. PCC 7116, *Stanieria cyanosphaera* PCC 7437, *Synechococcus elongatus* PCC 6301, *Synechococcus elongatus* PCC 7942, *Synechococcus* sp. CC9311, *Synechococcus* sp. CC9605, *Synechococcus* sp. CC9902, *Synechococcus* sp. JA-3-3Ab, *Synechococcus* sp. KORDI-100, *Synechococcus* sp. KORDI-49, *Synechococcus* sp. KORDI-52, *Synechococcus* sp. PCC 6312, *Synechococcus* sp. PCC 7002, *Synechococcus* sp. PCC 7502, *Synechococcus* sp. RCC307, *Synechococcus* sp. WH 7803, *Synechococcus* sp. WH 8103, *Synechococcus* sp. WH 8109, *Synechocystis* sp. PCC 6714, *Chlorogloeopsis fritschii* PCC6912 and *Thermosynechococcus elongatus* BP-1. The above list is not an all-inclusive list of candidate organisms; in fact, the above list only provides a partial list of photoautotrophic microbes that have been genetically sequenced in recent history, potentially facilitating the genetic transformation process required for heterologous expression of the enzymatic pathway.

As a preferred embodiment, and as reduced to practice, the photoautotrophic organism selected for the expression of the enzymatic pathway is *Synechocystis* sp. PCC 6803, as mentioned previously. The following two examples further detail reduction to practice of two specified organisms with characteristics within the scope of this patent.

EXAMPLES

Below are presented two examples reduced to practice as noted in the detailed description. Example 1 describes the generation of *Synechocystis* sp. PCC 6803 strain that is verified to display detoxifying activity towards microcystin-LR (hereafter: 6803mlrAsec+). In addition to displaying genetic stability, this strain shows prolonged activity when cultured in lake water compared to heterotrophic strains modified to express a homologous detoxifying enzymatic pathway. This strain (6803mlrAsec+) was transformed with a genetic cassette (described below) containing *Sphingomonas* sp. USTB-05 MlrA with a 23 amino acid N-terminal peptide tag consisting of: (from N-terminal) the first 21 amino acids of the *Synechocystis* sp. PCC 6803 PilA gene (sll1694) followed by a Methionine followed by a Glycine.

Example 2 describes a second *Synechocystis* sp. PCC 6803 strain transformed with a genetic cassette (described below) containing *Sphingomonas* sp. USTB-05 MlrA with no 23 amino acid N-terminal peptide tag. This construct was observed to be genetically unstable, and was thus unqualified for downstream analysis of MlrA activity.

Example 1—Generation and Analysis of 6803mlrAsec+

Genetic components described below were incorporated into a synthesized expression cassette targeting *Sphingopyxis* sp. USTB-05 mlrA, codon-optimized for expression in 6803, for double homologous recombination into the *Synechocystis* sp. PCC 6803 genome. The cassette utilizes the strong cpcB560 promoter to drive mlrA expression, flanking homologous recombination sequence for integration at the slr0271 genomic locus, and incorporation of the native PilA (sll1694) 5'-leader peptide sequence in an attempt to secrete MlrA enzyme into the extracellular space. Other features of the cassette are the aphAI kanamycin resistance gene for selection and the BBa_B0014 BioBrick bi-directional transcriptional terminator downstream of the mlrA gene. Additionally, the final base pair of the cpcB560 promoter was changed from A to C to allow for incorporation of an NcoI restriction enzyme site in the expression cassette.

The above 3749 bp expression cassette was synthesized and inserted into a pMV derivative (pMB1 ori, lacking requested restriction sites) by Beijing Genomics Institute (BGI) and supplied as both purified plasmid and an *E. coli* TOP10 plasmid-containing clone. The complete sequence (base pairs 1 to 5856) of this plasmid (p6803mlrAsec+) is provided as SEQ ID No: 1. The expression cassette responsible for the expression of MlrA within *Synechocystis* sp. PCC 6803 is located from base pair 182 to 3930. Within this region, specific features include the 5' homologous recombination site (base pairs 182 to 668 of SEQ ID No: 1), the aphAI kanamycin resistance gene (base pairs 675 to 1675 of SEQ ID No: 1), the cpcB560 promoter (base pairs 1682 to 2241 of SEQ ID No: 1), the PilA secretion tag (base pairs 2242 to 2310 of SEQ ID No: 1), the codon-optimized *Sphingopyxis* sp. USTB-05 mlrA (base pairs 2311 to 3321 of SEQ ID No: 1), BBa_B0014 terminator (base pairs 3328 to 3422 of SEQ ID No: 1), and the 3' homologous recombination site (base pairs 3431 to 3930 of SEQ ID No: 1). The above plasmid (p6803mlrAsec+) was transformed into *Synechocystis* sp. PCC 6803 via natural transformation followed by increased kanamycin selective pressure and clonal isolation of cells with complete segregation of genomes containing the desired double homologous recombination. This was accomplished as follows: *Synechocystis* sp. PCC 6803 was cultured in fresh BG-11 media from an optical density measured at 730 nanometers ($OD_{730}$) of 0.02-0.1 to an $OD_{730}$ of 0.8-1, cells were harvested via centrifugation at 4000 rpm for 10 min and washed 2 times with fresh BG-11. The cells were then concentrated to $OD_{730}$ of 10 and 100 μL of this cell suspension was mixed with 10 μL of p6803mlrAsec+ (at 166 ng $\mu L^{-1}$) and placed in the incubator under low light intensity for 16 hours. The mixture was then plated on BG-11 agar with kanamycin 5 μg $ml^{-1}$ and 20 mM glucose. After 7-15 days, single colonies were restreaked on BG-11 agar, kanamycin 20 μg $ml^{-1}$, 20 mM glucose. Single colonies from these agar cultures were then restreaked on BG-11 agar, kanamycin 50 μg $ml^{-1}$ (Km50), 20 mM glucose. Lawns from these single colonies on the Km50 BG-11 agar plates were then tested using a PCR assay to investigate segregation status at the targeted genomic locus, while simultaneously additional single colonies were selected and replated at the same selective pressure (Km50, if further chromosomal segregation is required), again subjecting the resultant lawn from these restreaks to the PCR assay.

PCR assay. The PCR assay for verification of the correct genotype consisted of the following process. A pipette tip was used to touch the lawn on the agar plate of the isolate to be investigated. The adhering cells were transferred to 10 μL ultrapure water, resuspended, and subjected to two freeze/thaw cycles before being used as the template in the PCR assay (1 μL). The PCR assay utilized primers 3FW/4REV (primer 3FW is given as SEQ ID No: 2, primer 4REV is given as SEQ ID No: 3) for analysis of the slr0271 locus to verify complete segregation of the double homologous recombinant, with the expected wild type (WT) amplicon being 704 base pairs (bp), and the amplicon with the insertion of the p6803mlrAsec+ expression cassette being 3040 bp. As a final confirmation and also as an indicator of stability, the PCR assay was repeated and the 3040 bp amplicon was confirmed via sequencing 126 days of continuous culturing after initial successful isolation of the 6803mlrAsec+ construct. When sent for sequencing, TAKARA PrimeSTAR HS DNA Polymerase was used in the PCR. PCR conditions were standard as directed by the manufacturer.

Expression of Recombinant MlrA in BL21(DE3) *E. coli*. Freshly transformed colonies of BL21(DE3) with the appropriate plasmid were inoculated into LB medium and grown at 37° C. until the optical density at 600 nanometers ($OD_{600}$) =0.8 was reached. In the experiments that required the induction of recombinant expression, the temperature was decreased to 30° C. when $OD_{600}$=0.6 was reached (approximately after 4 h) and IPTG (isopropyl β-D-thiogalactoside) at a final concentration of 1 mM was added; then, culturing was continued for 20 h. Subsequently, the bacteria were centrifuged (15000×g, 10 min, 4° C.), and the pellet was further processed, as described below.

For the assay with intact cells a fresh culture of *E. coli* BL21(DE3) was prepared by incubation in LB medium supplemented with ampicillin (100 μg $mL^{-1}$) for 24 h, until the $OD_{600}$ was in the range 1.5-2.0.

Cell Lysis and MlrA Activity Assay. Extracts of natural or heterologous MlrA expressing strains obtained by sonication using the ultrasonic processor UP50H/50W (Hielscher Ultrasonics) was used to estimate the MlrA activity against microcystin-LR (MC-LR). 300 μl of cell suspension was sonicated with a duty cycle 20 and 70% and amplitude 180 μm followed by intervals of 20 s for cooling. The number of cycles was between 3 and 15. After sonication, the extract was centrifuged at 12000 rpm. 10 μl of this extract in different dilutions was added to 90 μl of MC solution. To analyze the presence of MlrA outside the cells, 20 μl of cell suspension in PBS buffer with 180 μl of MC-LR solution was incubated for the appropriate periods and then samples were analyzed by HPLC. The cell extracts as well as MC-LR were suspended in phosphate buffer, pH 7.0. Final MC-LR concentration was 1 μg $mL^{-1}$. The incubation temperature was 20° C. and the reaction was stopped after 1 h by addition of 10 μl of 1% trifluoroacetic acid (TFA). Samples were cooled (4° C.) and analyzed by HPLC.

Experiments with Viable Cells of 6803mlrAsec+, *Sphingomonas* sp. ACM 3962 and *E. coli* BL21. To compare the potency of transformed cells to hydrolyze MC-LR, a degradation assay was performed for cultures of 6803mlrAsec+, *E. coli* BL21 and *Sphingomonas* sp. ACM 3962 (*Sphingomonas* sp.) as a natural, non-modified strain. 50 ml of the culture with $OD_{750}$=1 (6803mlrAsec+), or with $OD_{600}$=1 (for *E. coli* BL21 strains and *Sphingomonas* sp.), was washed twice with PBS. Cells were suspended in 300 μl of phosphate-buffered saline, pH 7.0 and incubated with MC-LR. After appropriate time of incubation (depending on the activity of different strains) cells were centrifuged and the reaction was stopped by the addition of TFA; samples were analyzed by HPLC. Simultaneously, to control for cell lysis and MlrA release 1 μg $mL^{-1}$ MC-LR solution was incubated with supernatant obtained after incubation of cell suspension.

The Activity of 6803mlrAsec+ and *E. coli* BL21_pET21-mlrA Against MC-LR in Semi-Natural Conditions. The MlrA activity of 6803mlrAsec+ and MlrA-expressing *E. coli* BL21 strains during extended incubation with waters from water reservoirs was compared. The 7 days and 1 day old cultures, respectively were inoculated in water from the local freshwater reservoir and incubated at 20° C., low light intensity (20 μmol of photons $m^{-2}$ $s^{-1}$) and gentle shaking. At initial time and after subsequent days a portion of cells was removed, centrifuged at 12000 rpm and analyzed for MlrA activity, as described previously.

HPLC Analyses. HPLC analyses were performed as described by Meriluoto and Spoof (Analysis of microcystins by high-performance liquid chromatography with photodiode-array detection. In *Toxic Cyanobacterial Monitoring and Cyanotoxin Analysis*; Meriluoto, J., Codd, G. A., Eds.; Abo Akademi University Press: Turku, Finland, 2005; pp 77-84. The methodology from the proceeding reference is incorporated herein) using an Agilent 1220 Infinity Gradient DAD LC System with a gradient pump and an integrated degassing unit, autosampler, column oven and diode array detector. MC-LR and its degradation product, acyclic MC-LR (acMC-LR) were separated and quantified using a Pursuit C18 RP-18 endcapped column. The mobile phase consisted of a gradient of 0.05% aqueous TFA (solvent A) and 0.05% TFA in acetonitrile (solvent B). The assays were performed with the following linear gradient program: 0 min 25% B, 5 min 70% B, 6 min 70% B, and 6.1 min 25% B. The retention times of MC-LR and acMC-LR were 3.7 and 3.2 min, respectively.

Strains and Growth Conditions. *Synechocystis* PCC 6803 (6803) was cultured using standard BG-11 media. Filter-sterilized glucose was added to the BG-11 agar media at 5 mM final concentration, unless otherwise noted. When culturing the cyanobacterial transformants kanamycin was supplemented at 50 μg $ml^{-1}$ final concentration. Erlenmeyer flasks (250 ml) were used with cyanobacterial working culture volumes of 40 ml, flasks were stoppered with gauze-wrapped cotton then topped with aluminum foil to facilitate gas exchange while preventing/reducing contamination, respectively. Liquid cultures were grown in an incubating shaker model BHWY-200 (Haishu Saifu Tset Instrument Factory, Ningbo, China) modified with the addition of a single 20 W fluorescent light (model T4-JL from Jinli Illumination, China) to provide sufficient irradiance for photoautotrophic growth. This light was arranged parallel to the linear arrangement of the (maximum of three) Erlenmeyer flasks within the incubating shaker, with a distance of approximately 7 cm from the naked bulb to the flask surface (widest point at base of flask). *Synechocystis* PCC 6803 cultures were grown at 28° C., 130 rpm, 24 h continuous light regime. Unless otherwise noted, cyanobacterial growth in liquid culture was monitored via spectrophotometric absorbance at 730 nm ($OD_{730}$) using a spectrophotometer (model T-6, Nanjing PHILES Instrument Company, China). BG-11 agar plates were incubated at 28° C. under continuous light (40% illumination intensity) in a lighted incubator (model PGX-350B, Haishu Saifu Tset Instrument Factory, Ningbo, China). *Escherichia coli* TOP10/DH5α for p6803mlrAsec+ plasmid propagation and for production of p6803mlrAsec− was grown using standard LB media and culturing protocols (37° C.), using ampicillin supplemented at 50 μg $ml^{-1}$ final concentration (Amp50), unless otherwise noted. Cyanobacterial liquid cultures were routinely tested for contamination by streaking on LB agar followed by incubation at 37° C. for 24-48 hours, followed by benchtop maintenance for continued monitoring (5 day) for development of fungal contamination. The cultures of *Synechocystis* PCC 6803 wild type and 6803mlrAsec+ used to establish MlrA activity were cultivated for 5-7 days in BG-11 medium, at 30° C. and 30 μmol of photons $m^{-2}$ $s^{-1}$. *Sphingomonas* sp. ACM-3962, obtained from Australian Collection of Microorganisms, was cultured in a recommended peptone yeast extract medium (10 g of peptone, 5 g NaCl, 5 g of yeast extract in 1 L of distilled water, pH 7.2) at 28° C. for 48 hours. After two days of incubation, cells were centrifuged and washed in PBS buffer. *Escherichia coli* DH5α and BL21(DE3) used for cloning, plasmid propagation and expression of MlrA recombinant proteins, were grown at 37° C. in LB broth supplemented with ampicilin (100 μg $mL^{-1}$), where indicated. The appropriate plasmid was transformed into *E. coli* BL21(DE3) and the bacteria were plated on LB agar plates supplemented with ampicillin (100 μg $mL^{-1}$).

Example 1—Results

FIG. 1 shows the gel electrophoresis results of the PCR assay indicating the successful isolation of *Synechocystis* sp. PCC 6803 colonies fully segregated for the presence of the MlrA expression cassette at the slr0271 genomic locus. Lane 1 (marked M) 1 kb DNA ladder (Lowest visible band in 1 kb ladder=1 kb, then 2 kb, 3 kb), lane 2 (marked +) positive control using p6803mlrAsec+ as PCR template, lanes 3-14 clonal isolates 1-12 (respectively), lane 15 (marked −) WT 6803 as negative control, lane 16 (marked C) no template as a negative control for the PCR reaction. Note the presence of the wild type amplicon at 704 bp (lane 15) and the presence of the 6803mlrAsec+ amplicon at 3040 bp (lane 2). Clonal isolates 9 and 10 (as marked) show complete segregation for 6803mlrAsec+ cassette integration. Isolate 10 was used for downstream analysis of MlrA activity in *Synechocystis* sp. PCC 6803. Isolate 10 (also referred to as 6803mlrAsec+) is the organism accepted and shown viable after submission to the China General Microbiological Culture Collection Center (CGMCC), at the CGMCC this organism is referred to as: 6803mlrAt. The deposition number at the CGMCC is: CGMCC No.: 13876. The sample was received and tested for viability on 12 Jun. 2017 (12-6-2017). The official letter from the CGMCC is dated 28 Jun. 2017 (28-6-2017). The address of the CGMCC is as given below:

China General Microbiological Culture Collection Center
Institute of Microbiology Chinese Academy of Sciences
NO. 1 West Beichen Road, Chaoyang District, Beijing 100101, China This submission to the CGMCC as detailed above is to fulfill the requirements of the Budapest Treaty.

The Expression and Activity of Recombinant MlrA. To express recombinant MlrA in 6803mlrAsec+ and *E. coli* BL21(DE3) the appropriate strains were cultivated in the condition described above. The lysate of 6803mlrAsec+ (A+ in TABLE 1) cells, similar to *E. coli* BL21(DE3) lysates, showed activity against MC-LR, whereas the wild type (WT) lysate was not active which confirms that the heterologous hosts produce MlrA (TABLE 1). No activity against MC-LR was detected in the extracellular medium from the culture of either WT *Synechocystis* sp. PCC 6803 or 6803mlrAsec+. The maximal detected MlrA activity after the lysis using sonication is also indicated in TABLE 1.

TABLE 1

The activity of MlrA in lysates and medium from the culture of wild type *Synechocystis* sp. PCC 6803 (WT) and 6803mlrAsec+ (A+) and the efficiency of MlrA extraction from the cells of 6803mlrAsec+. Activity is calculated per 1 mL of culture and $OD_{750}$ = 1.

| Sample | Type of cell lysis | MlrA activity (mU $mL^{-1}$) |
|---|---|---|
| WT lysate | Sonication | not detected |
| A+ lysate | Sonication | 46.5 ± 2.0 |
| WT medium | Sonication | not detected |
| A+ medium | Sonication | not detected |
| A+ lysate | Sonication, 3 cycles | 6.6 |
| | Sonication, 5 cycles | 14.5 |
| | Sonication, 10 cycles | 71.7 |
| | Sonication, 15 cycles | 148.3 |
| | Homogenisation | 42.1 |

In comparison with the other hosts (MlrA expressing *E. coli* strains BL21_pGEX-mlrA (MlrA-GST), BL21_pET21-mlrA (MlrA-HisTag), BL21_pGEX-mlrA (MlrA-GST-HisTag)) and native MlrA expressing cells (*Sphingomonas* sp.), the activity of 6803mlrAsec+ cell lysate lies between the highest and the lowest value (TABLE 2). MlrA activity in TABLE 2 results are normalized to 1 mL of culture and either $OD_{750=1}$ (for 6803mlrAsec+), or $OD_{600=1}$ (for *E. coli* BL21 strains and *Sphingomonas* sp.). TABLE 2 column 1 notes the strains, column 2 notes the MlrA activity of the cell lysate as described above, while column 3 notes the MlrA activity of the intact cells (whole cell culture).

The intact cells of 6803mlrAsec+ expressed the MlrA activity (TABLE 2, column 3) that was approximately one thousand-fold lower than the activity of lysates (TABLE 2, column 2). It was indicated, after normalization of these results on the respective optical density and volumetric bases during lag phase culture, that whole cells of 6803mlrAsec+ exhibited approximately 3 times higher MlrA activity than *Sphingomonas* cells.

TABLE 2

Comparison of MlrA activity between various hosts.

| Strain | MlrA activity (mU $mL^{-1}$) | |
|---|---|---|
| *Synechocystis* 6803mlrAsec+ | 148.3 ± 2.0 | 0.05 ± 0.02 |
| *Sphingomonas* sp. | n.a. | 0.02 ± 0.01 |
| BL21_pGEX-mlrA (MlrA-GST) | 113.7 ± 17.8 | 0.12 ± 0.03 |
| BL21_pET21-mlrA (MlrA-HisTag) | 773.9 ± 411 | n.a |
| BL21_pGEX-mlrA (MlrA-GST-HisTag) | 23.4 ± 4.8 | n.a |

Figure 2:
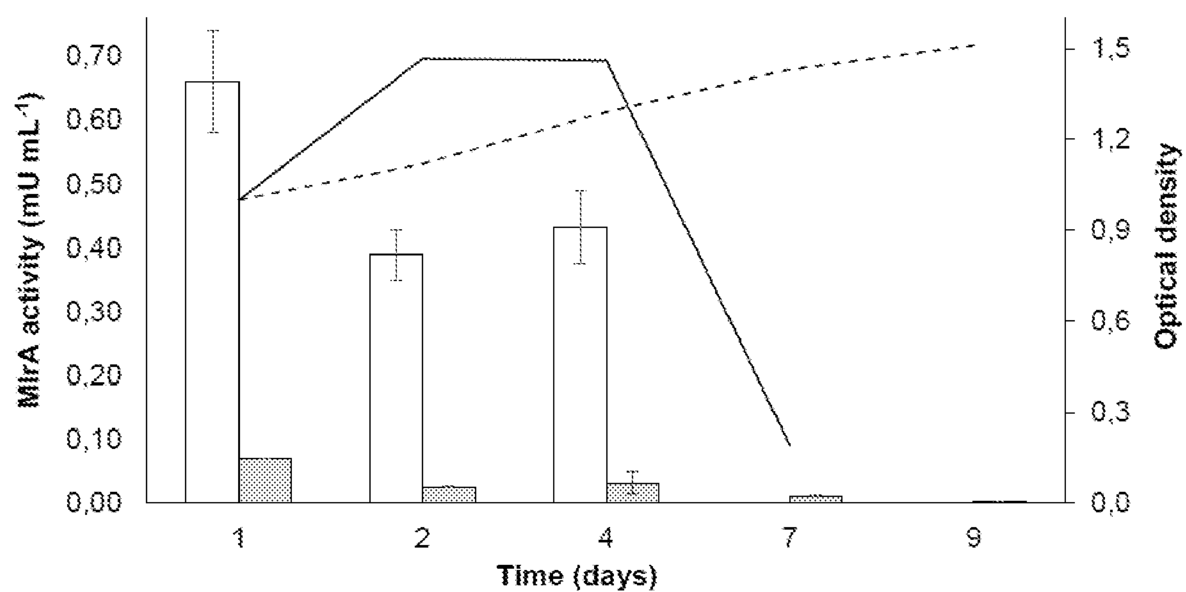

The Stability of MlrA Activity in Semi-Natural Conditions. During the long-term cultivation of 6803mlrAsec+ (15 d) the activity of both lysates and intact cells varied from 2-37 mU $mL^{-1}$ of culture (lysates) and 0.02-0.09 mU $mL^{-1}$ (intact cells). To examine the long-term activity of 6803mlrAsec+ against MC-LR, cells were inoculated into water sampled from a reservoir near Krakow, Poland. Simultaneously, *E. coli* BL21_pET21-mlrA was also incubated in the same conditions. The initial MlrA activity of *E. coli* was 9.4 times higher than 6803mlrAsec+. However, the activity of *E. coli* disappeared after 4 days of incubation, whereas cells of 6803mlrAsec+ were active after 9 days, although only 3% of the initial MlrA activity of 6803mlrAsec+ was preserved (FIG. 2). FIG. 2 shows MlrA activity (mU $mL^{-1}$) of 6803mlrAsec+ (grey blocs) and *E. coli* BL21_pET21-mlrA cultures (white blocs), along with $OD_{750}$ (6803mlrAsec+, dashed line) and $OD_{600}$ (*E. coli* BL21_pET21-mlrA, solid line) during extended incubation in water from said freshwater reservoir.

Note that an important feature of the proposed system is the photoautotrophic character of the host. This may provide several advantages when designing methods for biological-based water detoxification, especially relating to the stability of biocatalyst function and process cost/input per unit of degradative activity. The results from this short initial experiment (FIG. 2) indicate that the activity against microcystin is more stable in photoautotrophs in comparison to heterotrophic bacterial strains. Despite the lower initial MlrA activity, the culture of 6803MlrAsec+ showed the ability to detoxify MC-LR for a longer period compared to an MlrA-expressing *E. coli* strain. In addition, both the viability and cell density of the photoautotrophic host is maintained for a significantly longer period of time, as shown by the respective optical density measurements.

Example 2—Generation of 6803mlrAsec−

An attempt was made to express the native MlrA enzyme, with the N-terminus 23 amino acid PilA tag removed from the expression cassette. Generation of this plasmid was performed as follows. Plasmid 6803mlrAsec+ was used as the template to generate plasmid 6803mlrAsec− (p6803mlrAsec−), lacking the N-terminus PilA secretion peptide tag. TAKARA PrimeSTAR HS DNA Polymerase was used according to protocol with 5' phosphorylated primers 9FW/10REV to amplify the p6803mlrAsec+ plasmid excluding the PilA secretion peptide (primer 9FW is given as SEQ ID No: 4, primer 10REV is given as SEQ ID No: 5). Note that primer 10REV 5' terminus initiates with a thymine (T) base, this was an attempt to reconstitute the original cpcB560 promoter via primer-directed mutation. Recall that the cpcB560 promoter in the p6803mlrAsec+ synthetic construct used as the template has a C substituting the A of the 3' terminal base, allowing for the incorporation of a NcoI site. Thus, the design of primer 10REV seeks to reestablish the unmodified cpcB560 promoter. The PCR reaction was then subjected to 2 h digest with TAKARA DpnI for digestion of p6803mlrAsec+ template plasmid to reduce false positive background when screening *E. coli* transformants. The digestion was then gel purified and used in a T4 ligation reaction with the goal of self-ligating the ends of the primary linear fragment to generate p6803mlrAsec−. *E. coli* DH5α was then transformed via electroporation with this ligation reaction and cells were selected on LB agar with ampicillin added at final concentration 50 μg $ml^{-1}$ (Amp50). Single colonies were picked, restreaked, and a preliminary analysis was performed using the above-mentioned PCR assay employing primers 3FW/4REV. An *E. coli* isolate showing the correct amplicon size (2970 bp) was then miniprepped and plasmid p6803mlrAsec− was confirmed via sequencing of the entire expression cassette. Due to primer design, a single deletion of the 3' terminus base of the cpcB560 promoter was observed.

The Ribosomal Binding Site (RBS) calculator (De Novo DNA Inc.) available at the Salis Lab website was then used to calculate the Translation Initiation Rate (in procedure defined units) of (a) the native cpcB promoter/cpcB gene (as reference to the natural context)=1209.2, (b) the native cpcB promoter/mlrA gene=843.6, (c) cpcB promoter [with single bp deletion]/mlrA gene=1147.6. In all three instances, only 135 bp of the cpcB promoter upstream of the start codon was included in the analysis. With this result, the decision was made to move forward with the transformation of 6803 with the given p6803mlrAsec-construct (containing the deletion), under the assumption that the given construct would have MlrA expression sufficient for proof-of-principle. Comparable transformation of 6803 with p6803mlrAsec− produced between 1-2 orders of magnitude fewer single colonies than transformation with control plasmid pPSBAIIKS. In addition, the resulting PCR assay produced only a single candidate out of more than 30 selected colonies with the expected amplicon size (2970 bp). Other clones showed either the wild type amplicon, or various aberrant banding patterns, generally presenting as a primary amplicon at an incorrect size. The PCR assay amplicon of the single correct clone was sequenced which showed extensive deviations from the expected mlrA coding sequence. A second potentially correct clone (showing approximately the correct amplicon size with the PCR assay) was sequenced and was also found to contain multiple mutations. Based on these experiences, the 6803mlrAsec-construct was deemed not genetically stable and should not be included in downstream analysis. Given the great strength of the cpcB560 promoter and the genetic instability of MlrA overexpression with this promoter, use of a weaker constitutive promoter (such one of the weaker promoters from the J23 series of synthetic *E. coli* promoters) or use of an inducible promoter, such as the green-light inducible cpcG2 promoter (and its derivatives), is warranted.

The above examples detail methodologies relevant for investigating the function of microcystin-degrading enzymes expressed in cyanobacteria, other microbial photoautotrophs, and photoautotrophs in general. Furthermore, enzymatic pathways targeting other toxins related to harmful algal blooms may be expressed in cyanobacteria via simple modifications of the plasmids described here (simple substitution of the current enzyme genetic coding sequence with genes coding for enzymes targeting other toxins), followed by transformation and analysis of the resulting isolates with methods analogous to the above examples.

BRIEF DESCRIPTION OF IMAGES

FIG. 1 is an image (digital photograph) of a gel electrophoresis experiment showing the result of a PCR assay for verification of the isolation of 6803mlrAsec+.

FIG. 2 is a combined graph showing both MlrA activity of intact cells and respective optical density for both a heterotrophic organism expressing MlrA (*E. coli* BL21_pET21-mlrA) and a photoautotrophic organism expressing MlrA (6803mlrAsec+), during prolonged culturing in semi-natural conditions (water sampled from reservoir). The photoautotrophic organism is shown to have extended duration of MlrA activity compared to the heterotrophic organism.

BRIEF DESCRIPTION OF TABLES

TABLE 1 is comparing the MlrA activity of various cellular lysates (extracts) of both wild type *Synechocystis* sp. PCC 6803 and 6803mlrAsec+ (MlrA expressing *Synechocystis* sp. PCC 6803). This shows MlrA activity is only observed in the transformed isolate.

TABLE 2 is a comparison of the MlrA activities of both cellular extracts (column 2) and whole intact cells (column 3) between various native and heterologous MlrA-expressing bacteria.

The applicant declares that the respective sequences disclosed both in this description and in the corresponding sequence listing file DEXTERUSPTOResponsetoOct22OfficeAction_ST25.txt are identical.

The invention claimed is:

1. A method for the production of a MlrA enzyme capable of degrading toxins associated with and specific to harmful algal blooms comprising:

transforming a photoautotrophic organism with a heterologous gene encoding a MlrA enzyme comprising the amino acid sequence selected from the group consisting of SEQ ID NOs: 8, 9, 10, 11, 12, 13, and 14 and wherein said heterologous gene further encodes a 23 amino acid peptide tag consisting of the first 21 amino acid residues encoded by the *Synechocystis* sp. PCC 6803 gene (sll1694) followed by a methionine residue and a glycine residue to the N-terminus of said MlrA enzyme.

2. The method of claim 1, wherein said photoautotrophic organism is a member of the phylum Cyanobacteria.

3. The method of claim 2, wherein said photoautotrophic organism is *Synechocystis* sp. PCC 6803.

4. A photoautotrophic organism transformed with a heterologous gene encoding a MlrA enzyme comprising the amino acid sequence selected from the group consisting of SEQ ID NOs: 8, 9, 10, 11, 12, 13, and 14, wherein said photoautotrophic organism is capable of degrading at least one toxin selected from the group consisting of microcystins and nodularins, wherein said MlrA enzyme further comprises the addition of a 23 amino acid peptide tag consisting of the first 21 amino acid residues encoded by the *Synechocystis* sp. PCC 6803 gene (sll1694) followed by a methionine residue and a glycine residue to the N-terminus of said MlrA enzyme.

5. The photoautotrophic organism of claim 4, wherein said photoautotrophic organism is a member of the phylum Cyanobacteria.

6. The photoautotrophic organism of claim 5, wherein said Cyanobacteria is *Synechocystis* sp. PCC 6803.

* * * * *

SEQUENCE LISTING

```
<160> NUMBER OF SEQ ID NOS: 14

<210> SEQ ID NO 1
<211> LENGTH: 5856
<212> TYPE: DNA
<213> ORGANISM: Artificial Sequence
<220> FEATURE:
<223> OTHER INFORMATION: Plasmid p6803mlrAsec+
<220> FEATURE:
<221> NAME/KEY: slr0271 5' homologous recombination site
<222> LOCATION: (182)..(668)
<223> OTHER INFORMATION: From Synechocystis PCC6803 slr0271
<220> FEATURE:
<221> NAME/KEY: aphA1 kanamycin resistance gene
<222> LOCATION: (675)..(1675)
<220> FEATURE:
<221> NAME/KEY: cpcB560 promoter
<222> LOCATION: (1682)..(2241)
<223> OTHER INFORMATION: Synechocystis PCC6803 cpcB560 promoter
<220> FEATURE:
<221> NAME/KEY: PilA (sll1694) N-terminal secretion tag
<222> LOCATION: (2242)..(2310)
<223> OTHER INFORMATION: Synechocystis PCC6803 PilA (sll1694) secretion
      tag
<220> FEATURE:
<221> NAME/KEY: codon-optimized Sphingopyxis sp. USTB-05 mlrA
<222> LOCATION: (2311)..(3321)
<220> FEATURE:
<221> NAME/KEY: BBa_B0014 terminator
<222> LOCATION: (3328)..(3422)
<220> FEATURE:
<221> NAME/KEY: slr0271 3' homologous recombination site
<222> LOCATION: (3431)..(3930)
<223> OTHER INFORMATION: From Synechocystis PCC 6803

<400> SEQUENCE: 1

aaaaataaac aaataggggt tccgcgcaca tttccccgaa aagtgccacc tgacgtctaa      60

gaaaccatta ttatcatgac attaacctat aaaaataggc gtatcacgag gccctttcgt     120

tgtaaaacga cggccagtcg aaccacgcaa tgcgtctcga tccgcagtgt cttgcgtctc     180

tccgctgaat ttagtcaaca tcggggacac cctgcacatg tggtttgttt tagcaagggc     240

ttttagaaaa aaatgctcaa tctgaacatc tcccatgaca tttcgcttgg cgatcgccga     300

ggaggaggag gctaaactgt tcgtcttttt ggctttcacc acgtagataa cagtacgagt     360

tattgggtca ttgaattatt aacaatataa ctatttgctg atttttatac ttgcaaattt     420
```

```
tagatctaat tgtattagtc ttctatagta gaaatataag gaaatcaaat tttcaaattt    480
tcatcttgaa aaacataaaa tttattcatt atttgttaat cgttgcccca tcaatttgtc    540
gttaaaatgg ttaatagggc tagaagagcg aagtatttgt atttgccgaa aatttcagga    600
gcaaaacaat gcgaatcaac cataagcctc tattaattgc cactgcctta ctaactctcg    660
tgcccaatga gctcacccat gttatattgc acaagataaa aatatatcat catgaacaat    720
aaaactgtct gcttacataa acagtaatac aaggggtgtt atgagccata ttcaacggga    780
aacgtcttgc tcgaggccgc gattaaattc caacctggat gctgatttat atgggtatag    840
atgggctcgc gataatgtcg ggcaatcagg tgcgacaatc tatcgattgt atgggaagcc    900
caatgcgcca gagttgtttc tgaaacatgg caaaggtagc gttgccaatg atgttacaga    960
tgagatggtc agactaaact ggctgacggc atttatgcct cttccgacca tcaagcattt   1020
tatccgtact cctgatgatg catggttact caccactgcg atccccggga aaacagcatt   1080
ccaggtatta gaagaatatc ctgattcagg tgaaaatatt gttgatgcgc tggcagtgtt   1140
cctgcgccgg ttgcattcga ttcctgtttg taattgtcct tttaacagcg atcgcgtatt   1200
tcgtctcgct caggcgcaat cacgaatgaa taacggtttg gttgatgcta gtgattttga   1260
tgacgagcgt aatggctggc ctgttgaaca agtctggaaa gaaatgcata agcttttgcc   1320
attctcaccg gattcagtcg tcactcatgg tgatttctca cttgataacc ttatttttga   1380
cgaggggaaa ttaataggtt gtattgatgt tggacgagtc ggaatcgcag accgatacca   1440
ggatcttgcc atcctatgga actgcctcgg tgagttttct ccttcattac agaaacggct   1500
ttttcaaaaa tatggtattg ataatcctga tatgaataaa ttgcagtttc atttgatgct   1560
cgatgagttt ttctgatagt tagtctttgt agagacacaa acctgaaatt ccggacaccg   1620
cgcttcagga catctccctg gacgccgata tctggcagta tccggacggt actatctgca   1680
gacctgtaga gaagagtccc tgaatatcaa aatggtggga taaaaagctc aaaaaggaaa   1740
gtaggctgtg gttccctagg caacagtctt ccctacccca ctggaaacta aaaaaacgag   1800
aaaagttcgc accgaacatc aattgcataa ttttagccct aaaacataag ctgaacgaaa   1860
ctggttgtct tcccttccca atccaggaca atctgagaat cccctgcaac attacttaac   1920
aaaaaagcag gaataaaatt aacaagatgt aacagacata agtcccatca ccgttgtata   1980
aagttaactg tgggattgca aaagcattca agcctaggcg ctgagctgtt tgagcatccc   2040
ggtggccctt gtcgctgcct ccgtgtttct ccctggattt atttaggtaa tatctctcat   2100
aaatccccgg gtagttaacg aaagttaatg gagatcagta acaataactc tagggtcatt   2160
actttggact ccctcagttt atccggggga attgtgttta agaaaatccc aactcataaa   2220
gtcaagtagg agattaattc catggctagt aattttaaat tcaaactcct ctctcaactc   2280
tccaaaaaac gggcagaagg tggtatgggg atgcgcgaat tcgtgaaaca acggcctctg   2340
ttatgttttt atgctctggc tatcctgatt gccttggccg cccatgccct gcgtgctatg   2400
agccccaccc ctctgggtcc tatgtttaaa atgctgcaag aaactcatgc ccatttgaac   2460
attatcaccg cggttcggag cactttcgaa tatcctggcg cttacaccct gctgctgttt   2520
cctgcggccc ctatgtttgc cgctttaatt gtgaccggca ttggttatgg ccgtgctggt   2580
tttcgcgaac tgttgtcccg ttgtgcccct tggcgtagtc ctgttagctg gcgtcaaggt   2640
gtgaccgtga ttgccgtttg ttttctggct ttttttgcgt tgaccggcat tatgtgggtg   2700
caaacgttta tctatgctcc tcccggcacc ttggatcgta ccttcctgcg ctatggctcc   2760
gaccctctgg ccatttacgc gatgttagcc gcttccttgc tgctgagtcc tggtcctctg   2820
```

```
ttagaagaat tgggttggcg cggctttgcc ttacctcaat tgctgaaaaa attcgatcct   2880
ctggctgccg cggtgatttt gggcctgatg tggtgggcct ggcatttacc ccgcgacttg   2940
cctaccctgt tttccggcga acctggcgcg gcgtggggcg tcattgtgaa acaatttgtg   3000
attattcccg gttttattgc tggcaccatt attgctgttt ttgtgtgtaa caaactgggc   3060
ggttccatgt ggggcggtgt gctgattcat gcgatccaca atgaattagg cgtgaatgtt   3120
accgctgaat gggcccccac cgtggccggt ctgggctggc gcccctggga tttagttgaa   3180
tttgccgtgg ccattggtct ggttctgatc tgtggtcgca gcttgggtgc tgccagtcct   3240
gataatgccc gcctggcgtg gggtaatgtt cctcctaaat tacccggtgt tgccaccgat   3300
aaaagtggtg cgaatgcgta gggatcctca cactggctca ccttcgggtg ggcctttctg   3360
cgtttatata ctagagagag aatataaaaa gccagattat taatccggct tttttattat   3420
ttgcggccgc tctttacaat ggccaggtct ttagggagcg gtgaccaacg accaaataat   3480
ttaatttttc caattatttt gatagttatt tggggaacat ggacgaataa aattcggata   3540
aaaagttaaa tttttctaat tctatagtcg ggttttcac ctatgactac tcccgttttt    3600
tgtactaatt gtggcaaccg ccttagcccc caggttcgtt tctgtgaatc ctgtggatgt   3660
cccgttgcct tgacgtcgga gccaccttcc ttttctggac caccattgtc cccattgcct   3720
cctccccctc ccacctttaa tgtcgatgaa gttccatccc ataaaagagg ggtaactcct   3780
tggattcctt ttttcctgtt atttagttct gtcgttgtat tagggggact ttggtggttg   3840
ggagcgttca atctgcccca atggaatcaa tggctagtaa aaattttgcc caccaatacc   3900
agttcccccg ttgttacttc ccctactccg agagacggag tcactgccaa ccgagacggt   3960
catagctgtt tcctgtgtgc cgcttcctcg ctcactgact cgctgcgctc ggtcgttcgg   4020
ctgcggcgag cggtatcagc tcactcaaag gcggtaatac ggttacccac agaatcaggg   4080
gataacgcag gaaagaacat gtgagcaaaa ggccagcaaa aggccaggaa ccgtaaaaag   4140
gccgcgttgc tggcgttttt ccataggctc cgcccccctg acgagcatca caaaaatcga   4200
cgctcaagtc agaggtggcg aaacccgaca ggactataaa gataccaggc gtttccccct   4260
ggaagctccc tcgtgcgctc tcctgttccg accctgccgc ttaccggata cctgtccgcc   4320
tttctccctt cgggaagcgt ggcgctttct catagctcac gctgtaggta tctcagttcg   4380
gtgtaggtcg ttcgctccaa gctgggctgt gtgcacgaac cccccgttca gcccgaccgc   4440
tgcgccttat ccggtaacta tcgtcttgag tccaacccgg taagacacga cttatcgcca   4500
ctggcagcag ccactggtaa caggattagc agagcgaggt atgtaggcgg tgctacagag   4560
ttcttgaagt ggtggcctaa ctacggctac actagaagga cagtatttgg tatctgcgct   4620
ctgctgaagc cagttacctt cggaaaaaga gttggtagct cttgatccgg caaacaaacc   4680
accgctggta gcggtggttt ttttgtttgc aagcagcaga ttacgcgcag aaaaaaagga   4740
tctcaagaag atcctttgat cttttctacg gggtctgacg ctcagtggaa cgaaaactca   4800
cgttaaggga ttttggtcat gagattatca aaaaggatct tcacctagat ccttttaaat   4860
taaaaatgaa gttttaaatc aatctaaagt atatatgagt aaacttggtc tgacagttac   4920
caatgcttaa tcagtgaggc acctatctca gcgatctgtc tatttcgttc atccatagtt   4980
gcctgactcc ccgtcgtgta gataactacg atacgggagg gcttaccatc tggccccagt   5040
gctgcaataa taccgcggga cccacgctca ccggctccag atttatcagc aataaaccag   5100
ccagccggaa gggccgagcg cagaagtggt cctgcaactt tatccgcctc catccagtct   5160
```

```
attaattgtt gccgggaagc tagagtaagt agttcgccag ttaatagttt gcgcaacgtt   5220

gttgccatcg ctacaggcat cgtggtatca cgctcgtcgt ttggtatggc ttcattcagc   5280

tccggttccc aacgatcaag gcgagttaca tgatccccca tgttgcgcaa aaaagcggtt   5340

agctccttcg gtcctccgat cgttgtcaga agtaagttgg ccgccgtgtt atcactcatg   5400

gttatggcag cactacataa ttctcttact gtcatgccat ccgtaagatg cttttctgtg   5460

actggtgagt actcaaccaa gtcattctga gaatagtgta tgcggcgacc gagttgctct   5520

tgcccggcgt caatacggga taataccgcg ccacatagca gaactttaaa agtgctcatc   5580

attggaaaac gttcttcggg gcgaaaactc tcaaggatct taccgctgtt gagatccagt   5640

tcgatgtaac ccactcgtgc acccaactga tcttcagcat cttttacttt caccagcgtt   5700

tctgggtgag caaaaacagg aaggcaaaat gccgcaaaaa agggaataag ggcgacacgg   5760

aaatgttgaa tactcatact cttccttttt caatattatt gaagcattta tcagggttat   5820

tgtctcatga gcggatacat atttgaatgt atttag                             5856


<210> SEQ ID NO 2
<211> LENGTH: 20
<212> TYPE: DNA
<213> ORGANISM: Artificial Sequence
<220> FEATURE:
<223> OTHER INFORMATION: primer 3FW

<400> SEQUENCE: 2

agggctagaa gagcgaagta                                                 20


<210> SEQ ID NO 3
<211> LENGTH: 21
<212> TYPE: DNA
<213> ORGANISM: Artificial Sequence
<220> FEATURE:
<223> OTHER INFORMATION: primer 4REV

<400> SEQUENCE: 3

acgggagtag tcataggtga a                                               21


<210> SEQ ID NO 4
<211> LENGTH: 22
<212> TYPE: DNA
<213> ORGANISM: Artificial Sequence
<220> FEATURE:
<223> OTHER INFORMATION: primer 9FW

<400> SEQUENCE: 4

atgcgcgaat tcgtgaaaca ac                                              22


<210> SEQ ID NO 5
<211> LENGTH: 30
<212> TYPE: DNA
<213> ORGANISM: Artificial Sequence
<220> FEATURE:
<223> OTHER INFORMATION: primer 10REV

<400> SEQUENCE: 5

tgaattaatc tcctacttga ctttatgagt                                      30


<210> SEQ ID NO 6
<211> LENGTH: 6
<212> TYPE: PRT
<213> ORGANISM: Sphingopyxis sp. USTB-05
<220> FEATURE:
<221> NAME/KEY: METAL
```

```
<222> LOCATION: (1)..(6)
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 6

His Xaa Xaa His Xaa Glu
1               5


<210> SEQ ID NO 7
<211> LENGTH: 6
<212> TYPE: PRT
<213> ORGANISM: Sphingopyxis sp. USTB-05

<400> SEQUENCE: 7

His Ala Ile His Asn Glu
1               5


<210> SEQ ID NO 8
<211> LENGTH: 336
<212> TYPE: PRT
<213> ORGANISM: Sphingopyxis sp. C-1

<400> SEQUENCE: 8

Met Arg Glu Phe Val Lys Gln Arg Pro Leu Leu Cys Phe Tyr Ala Leu
1               5                   10                  15

Ala Ile Leu Ile Ala Leu Thr Ala His Ala Leu Arg Ala Met Ser Pro
            20                  25                  30

Thr Pro Leu Gly Pro Met Phe Lys Met Leu Gln Glu Thr His Ala His
        35                  40                  45

Leu Asn Ile Ile Thr Ala Val Arg Ser Thr Phe Asp Tyr Pro Gly Ala
    50                  55                  60

Tyr Thr Leu Leu Leu Phe Pro Ala Ala Pro Met Leu Ala Ala Leu Ile
65                  70                  75                  80

Val Thr Gly Ile Gly Tyr Gly Arg Ser Gly Phe Arg Glu Leu Leu Ser
                85                  90                  95

Arg Cys Ala Pro Trp Arg Ser Pro Val Ser Trp Arg Gln Gly Val Thr
            100                 105                 110

Val Ile Ala Val Cys Phe Leu Ala Phe Phe Ala Leu Thr Gly Ile Met
        115                 120                 125

Trp Val Gln Thr Tyr Leu Tyr Ala Pro Pro Gly Thr Leu Asp Arg Thr
    130                 135                 140

Phe Leu Arg Tyr Gly Ser Asp Pro Val Ala Ile Tyr Met Met Leu Ala
145                 150                 155                 160

Ala Ser Leu Leu Leu Ser Pro Gly Pro Leu Leu Glu Glu Leu Gly Trp
                165                 170                 175

Arg Gly Phe Ala Leu Pro Gln Leu Leu Lys Lys Phe Asp Pro Leu Ala
            180                 185                 190

Ala Ala Val Ile Leu Gly Leu Met Trp Trp Ala Trp His Leu Pro Arg
        195                 200                 205

Asp Leu Pro Thr Leu Phe Ser Gly Glu Pro Gly Ala Ala Trp Gly Val
    210                 215                 220

Ile Val Lys Gln Phe Val Ile Ile Pro Gly Phe Ile Ala Gly Thr Ile
225                 230                 235                 240
```

```
Ile Ala Val Phe Val Cys Asn Lys Leu Gly Gly Ser Met Trp Gly Gly
                245                 250                 255

Val Leu Ile His Ala Ile His Asn Glu Leu Gly Val Asn Val Thr Ala
            260                 265                 270

Glu Trp Ala Pro Thr Val Ala Gly Leu Gly Trp Arg Pro Trp Asp Leu
        275                 280                 285

Val Glu Phe Ala Val Ala Ile Gly Leu Val Leu Ile Cys Gly Arg Ser
    290                 295                 300

Leu Gly Ala Ala Ser Pro Asp Asn Ala Arg Leu Ala Trp Gly Asn Val
305                 310                 315                 320

Pro Pro Lys Leu Pro Gly Gly Ala Thr Asp Lys Ser Gly Ala Asn Ala
                325                 330                 335


<210> SEQ ID NO 9
<211> LENGTH: 336
<212> TYPE: PRT
<213> ORGANISM: Sphingopyxis sp.

<400> SEQUENCE: 9

Met Arg Glu Phe Val Lys Gln Arg Pro Leu Leu Cys Phe Tyr Ala Leu
1               5                   10                  15

Ala Ile Leu Ile Ala Leu Ala Ala His Ala Leu Arg Ala Met Ser Pro
            20                  25                  30

Thr Pro Leu Gly Pro Met Phe Lys Met Leu Gln Glu Thr His Ala His
        35                  40                  45

Leu Asn Ile Ile Thr Ala Val Arg Ser Thr Phe Glu Tyr Pro Gly Ala
    50                  55                  60

Tyr Thr Leu Leu Leu Phe Pro Ala Ala Pro Met Phe Ala Ala Leu Ile
65                  70                  75                  80

Val Thr Gly Ile Gly Tyr Gly Arg Ala Gly Phe Arg Glu Leu Leu Ser
                85                  90                  95

Arg Cys Ala Pro Trp Arg Ser Pro Val Ser Trp Arg Gln Gly Val Thr
            100                 105                 110

Val Ile Ala Val Cys Phe Leu Ala Phe Phe Ala Leu Thr Gly Ile Met
        115                 120                 125

Trp Val Gln Thr Phe Ile Tyr Ala Pro Pro Gly Thr Leu Asp Arg Thr
    130                 135                 140

Phe Leu Arg Tyr Gly Ser Asp Pro Leu Ala Ile Tyr Ala Met Leu Ala
145                 150                 155                 160

Ala Ser Leu Leu Leu Ser Pro Gly Pro Leu Leu Glu Glu Leu Gly Trp
                165                 170                 175

Arg Gly Phe Ala Leu Pro Gln Leu Leu Lys Lys Phe Asp Pro Leu Ala
            180                 185                 190

Ala Ala Val Ile Leu Gly Leu Met Trp Trp Ala Trp His Leu Pro Arg
        195                 200                 205

Asp Leu Pro Thr Leu Phe Ser Gly Glu Pro Gly Ala Ala Trp Gly Val
    210                 215                 220

Ile Val Lys Gln Phe Val Ile Ile Pro Gly Phe Ile Ala Gly Thr Ile
225                 230                 235                 240

Ile Ala Val Phe Val Cys Asn Lys Leu Gly Gly Ser Met Trp Gly Gly
                245                 250                 255

Val Leu Ile His Ala Ile His Asn Glu Leu Gly Val Asn Val Thr Ala
            260                 265                 270

Glu Trp Ala Pro Thr Val Ala Gly Leu Gly Trp Arg Pro Trp Asp Leu
        275                 280                 285
```

```
Val Glu Phe Ala Val Ala Ile Gly Leu Val Leu Ile Cys Gly Arg Ser
    290                 295                 300

Leu Gly Ala Ala Ser Pro Asp Asn Ala Arg Leu Ala Trp Gly Asn Val
305                 310                 315                 320

Pro Pro Lys Leu Pro Gly Val Ala Thr Asp Lys Ser Gly Ala Asn Ala
                325                 330                 335


<210> SEQ ID NO 10
<211> LENGTH: 336
<212> TYPE: PRT
<213> ORGANISM: Sphingopyxis sp. MB-E

<400> SEQUENCE: 10

Met Arg Glu Phe Val Lys Gln Arg Pro Leu Leu Cys Phe Tyr Ala Leu
1               5                   10                  15

Ala Ile Leu Ile Ala Leu Ala Ala His Ala Leu Arg Ala Met Ser Pro
            20                  25                  30

Thr Pro Leu Gly Pro Met Phe Lys Met Leu Gln Glu Thr His Ala His
        35                  40                  45

Leu Asn Ile Ile Thr Ala Val Arg Ser Thr Phe Glu Tyr Pro Gly Ala
    50                  55                  60

Tyr Thr Leu Leu Leu Phe Pro Ala Ala Pro Met Phe Ala Ala Leu Ile
65                  70                  75                  80

Val Thr Gly Ile Gly Tyr Gly Arg Ala Gly Phe Arg Glu Leu Leu Ser
                85                  90                  95

Arg Cys Ala Pro Trp Arg Ser Pro Val Ser Trp Arg Gln Gly Val Thr
            100                 105                 110

Val Ile Ala Val Cys Phe Leu Ala Phe Phe Ala Leu Thr Gly Ile Met
        115                 120                 125

Trp Val Gln Thr Phe Ile Tyr Ala Pro Pro Gly Thr Leu Asp Arg Thr
    130                 135                 140

Phe Leu Arg Tyr Gly Ser Asp Pro Leu Ala Ile Tyr Ala Met Leu Ala
145                 150                 155                 160

Ala Ser Leu Leu Leu Ser Pro Gly Pro Leu Leu Glu Glu Leu Gly Trp
                165                 170                 175

Arg Gly Phe Ala Leu Pro Gln Leu Leu Lys Lys Phe Asp Pro Leu Ala
            180                 185                 190

Ala Ala Val Ile Leu Gly Leu Met Trp Trp Ala Trp His Leu Pro Arg
        195                 200                 205

Asp Leu Pro Thr Leu Phe Ser Gly Glu Pro Gly Ala Ala Trp Gly Val
    210                 215                 220

Ile Val Lys Gln Phe Val Ile Ile Pro Ala Phe Ile Ala Gly Thr Ile
225                 230                 235                 240

Ile Ala Val Phe Val Cys Asn Lys Leu Gly Gly Ser Met Trp Gly Gly
                245                 250                 255

Val Leu Ile His Ala Ile His Asn Glu Leu Gly Val Asn Val Thr Ala
            260                 265                 270

Glu Trp Ala Pro Thr Val Ala Gly Leu Gly Trp Arg Pro Trp Asp Leu
        275                 280                 285

Val Glu Phe Ala Val Ala Ile Gly Leu Val Leu Ile Cys Gly Arg Ser
    290                 295                 300

Leu Gly Ala Ala Ser Pro Asp Asn Ala Arg Leu Ala Trp Gly Asn Val
305                 310                 315                 320

Pro Pro Lys Leu Pro Gly Val Ala Thr Asp Lys Ser Gly Ala Asn Ala
```

325 330 335

<210> SEQ ID NO 11
<211> LENGTH: 336
<212> TYPE: PRT
<213> ORGANISM: Sphingomonas sp. ACM-3962

<400> SEQUENCE: 11

Met Arg Glu Phe Val Arg Gln Arg Pro Leu Leu Cys Phe Tyr Val Leu
1 5 10 15

Ala Ile Leu Ile Ala Leu Ala Ala His Ala Leu Arg Ala Met Ser Pro
20 25 30

Thr Pro Leu Asp Pro Met Phe Lys Met Leu Gln Glu Thr His Ala His
35 40 45

Leu Asn Ile Ile Thr Ala Val Arg Ser Thr Phe Glu Tyr Pro Gly Ala
50 55 60

Tyr Thr Leu Leu Leu Phe Pro Ala Ala Pro Met Phe Ala Ala Leu Ile
65 70 75 80

Ala Thr Gly Ile Gly Tyr Gly Gln Ala Gly Phe Arg Glu Leu Leu Ser
85 90 95

Arg Cys Ala Pro Trp Arg Ser Pro Val Ser Trp Arg Gln Gly Val Thr
100 105 110

Val Ile Ala Val Cys Phe Leu Ala Phe Phe Ala Leu Thr Gly Ile Met
115 120 125

Trp Val Gln Thr Tyr Leu Tyr Ala Pro Pro Gly Thr Leu Asp Arg Thr
130 135 140

Phe Leu Arg Tyr Gly Ser Asp Pro Val Ala Ile Tyr Val Met Leu Ala
145 150 155 160

Ala Ser Leu Leu Leu Ser Pro Gly Pro Leu Leu Glu Glu Leu Gly Trp
165 170 175

Arg Gly Phe Ala Leu Pro Gln Leu Leu Lys Lys Phe Asp Pro Leu Thr
180 185 190

Ala Ala Val Ile Leu Gly Ile Met Trp Trp Ala Trp His Leu Pro Arg
195 200 205

Asp Leu Pro Thr Leu Phe Ser Gly Ala Pro Gly Ala Ala Trp Ser Val
210 215 220

Ile Val Lys Gln Leu Val Ile Thr Pro Gly Phe Ile Ala Ser Thr Ile
225 230 235 240

Ile Ala Val Phe Val Cys Asn Lys Leu Gly Gly Ser Met Trp Gly Gly
245 250 255

Val Leu Thr His Ala Ile His Asn Glu Leu Gly Val Asn Val Thr Ala
260 265 270

Glu Trp Ala Pro Thr Val Ala Gly Leu Gly Trp Arg Pro Trp Asp Leu
275 280 285

Ile Glu Phe Ala Val Ala Ile Gly Leu Val Leu Ile Cys Gly Arg Ser
290 295 300

Leu Gly Ala Ala Ser Pro Asp Asn Ala Arg Leu Ala Trp Gly Asn Val
305 310 315 320

Pro Pro Lys Leu Pro Gly Gly Val Gly Asp Lys Ser Gly Ala Asn Ala
325 330 335

<210> SEQ ID NO 12
<211> LENGTH: 336
<212> TYPE: PRT
<213> ORGANISM: Novosphingobium sp. THN1

<400> SEQUENCE: 12

```
Met Arg Glu Phe Val Arg Gln Arg Pro Leu Leu Cys Leu Tyr Val Leu
1               5                   10                  15

Ala Ile Leu Ile Ala Leu Ala Ala His Ala Leu Arg Ala Met Ser Pro
            20                  25                  30

Thr Pro Leu Asp Pro Met Phe Lys Met Leu Gln Glu Thr His Ala His
        35                  40                  45

Leu Asn Ile Ile Thr Ala Val Arg Ser Thr Phe Glu Tyr Pro Gly Ala
    50                  55                  60

Tyr Thr Leu Leu Leu Phe Pro Ala Ala Pro Met Phe Ala Ala Leu Ile
65                  70                  75                  80

Ala Thr Gly Ile Gly Tyr Gly Gln Ala Gly Phe Arg Glu Leu Leu Ser
                85                  90                  95

Arg Cys Ala Pro Trp Arg Ser Pro Val Ser Trp Arg Gln Gly Val Thr
            100                 105                 110

Val Ile Ala Val Cys Phe Leu Ala Phe Phe Ala Leu Thr Gly Ile Met
        115                 120                 125

Trp Val Gln Thr Tyr Leu Tyr Ala Pro Pro Gly Thr Leu Asp Arg Thr
    130                 135                 140

Phe Leu Arg Tyr Gly Ser Asp Pro Val Ala Ile Tyr Val Met Leu Ala
145                 150                 155                 160

Ala Ser Leu Leu Leu Ser Pro Gly Pro Leu Leu Glu Glu Leu Gly Trp
                165                 170                 175

Arg Gly Phe Ala Leu Pro Gln Leu Leu Lys Lys Phe Asp Pro Leu Thr
            180                 185                 190

Ala Ala Val Ile Leu Gly Ile Met Trp Trp Ala Trp His Leu Pro Arg
        195                 200                 205

Asp Leu Pro Thr Leu Phe Ser Gly Ala Pro Gly Ala Ala Trp Ser Val
    210                 215                 220

Ile Val Lys Gln Leu Val Ile Ala Pro Gly Phe Ile Ala Ser Thr Ile
225                 230                 235                 240

Ile Ala Val Phe Val Cys Asn Lys Leu Gly Gly Ser Met Trp Gly Gly
                245                 250                 255

Val Leu Thr His Ala Ile His Asn Glu Leu Gly Val Asn Val Thr Ala
            260                 265                 270

Glu Trp Ala Pro Thr Val Ala Gly Ile Gly Trp Arg Pro Trp Asp Leu
        275                 280                 285

Ile Glu Phe Ala Val Ala Ile Gly Leu Val Leu Ile Cys Gly Arg Ser
    290                 295                 300

Leu Gly Ala Ala Ser Pro Asp Asn Ala Arg Leu Ala Trp Gly Asn Val
305                 310                 315                 320

Pro Pro Lys Leu Pro Gly Gly Val Gly Asp Lys Ser Gly Ser Asn Ala
                325                 330                 335
```

<210> SEQ ID NO 13
<211> LENGTH: 336
<212> TYPE: PRT
<213> ORGANISM: Sphingomonas sp. USTB-05

<400> SEQUENCE: 13

```
Met Arg Glu Phe Val Lys Gln Arg Pro Leu Leu Cys Phe Tyr Ala Leu
1               5                   10                  15

Ala Ile Leu Ile Ala Leu Ala Ala His Ala Leu Arg Ala Met Ser Pro
            20                  25                  30
```

```
Thr Pro Leu Gly Pro Met Phe Lys Met Leu Gln Glu Thr His Ala His
        35                  40                  45

Leu Asn Ile Ile Thr Ala Val Arg Ser Thr Phe Glu Tyr Pro Gly Ala
    50                  55                  60

Tyr Thr Leu Leu Leu Phe Pro Ala Ala Pro Met Phe Ala Ala Leu Ile
65                  70                  75                  80

Val Thr Gly Ile Gly Tyr Gly Arg Ala Gly Phe Arg Glu Leu Leu Ser
                85                  90                  95

Arg Cys Ala Pro Trp Arg Ser Pro Val Ser Trp Arg Gln Gly Val Thr
            100                 105                 110

Val Ile Ala Val Cys Phe Leu Ala Phe Phe Ala Leu Thr Gly Ile Met
        115                 120                 125

Trp Val Gln Thr Phe Ile Tyr Ala Pro Pro Gly Thr Leu Asp Arg Thr
    130                 135                 140

Phe Leu Arg Tyr Gly Ser Asp Pro Leu Ala Ile Tyr Ala Met Leu Ala
145                 150                 155                 160

Ala Ser Leu Leu Leu Ser Pro Gly Pro Leu Leu Glu Glu Leu Gly Trp
                165                 170                 175

Arg Gly Phe Ala Leu Pro Gln Leu Leu Lys Lys Phe Asp Pro Leu Ala
            180                 185                 190

Ala Ala Val Ile Leu Gly Leu Met Trp Trp Ala Trp His Leu Pro Arg
        195                 200                 205

Asp Leu Pro Thr Leu Phe Ser Gly Glu Pro Gly Ala Ala Trp Gly Val
    210                 215                 220

Ile Val Lys Gln Phe Val Ile Ile Pro Gly Phe Ile Ala Gly Thr Ile
225                 230                 235                 240

Ile Ala Val Phe Val Cys Asn Lys Leu Gly Gly Ser Met Trp Gly Gly
                245                 250                 255

Val Leu Ile His Ala Ile His Asn Glu Leu Gly Val Asn Val Thr Ala
            260                 265                 270

Glu Trp Ala Pro Thr Val Ala Gly Leu Gly Trp Arg Pro Trp Asp Leu
        275                 280                 285

Val Glu Phe Ala Val Ala Ile Gly Leu Val Leu Ile Cys Gly Arg Ser
    290                 295                 300

Leu Gly Ala Ala Ser Pro Asp Asn Ala Arg Leu Ala Trp Gly Asn Val
305                 310                 315                 320

Pro Pro Lys Leu Pro Gly Val Ala Thr Asp Lys Ser Gly Ala Asn Ala
                325                 330                 335


<210> SEQ ID NO 14
<211> LENGTH: 336
<212> TYPE: PRT
<213> ORGANISM: Rhizobium sp. TH

<400> SEQUENCE: 14

Met Arg Glu Phe Val Arg Gln Arg Pro Leu Val Ser Phe Tyr Val Leu
1               5                   10                  15

Ala Ile Leu Ile Ala Leu Ala Ala Asn Val Leu Arg Ala Met Asp Pro
            20                  25                  30

Thr Pro Leu Gly Pro Met Phe Lys Met Leu Gln Glu Thr His Ala His
        35                  40                  45

Leu Asn Ile Val Thr Ala Ile Arg Ser Thr Phe Asp Tyr Pro Thr Ala
    50                  55                  60

Tyr Thr Phe Leu Leu Phe Pro Ala Ala Pro Met Leu Ala Ala Leu Ile
65                  70                  75                  80
```

-continued

```
Val Thr Gly Ile Gly Tyr Gly Arg Ala Gly Phe Arg Glu Leu Leu Ser
                85                  90                  95

Arg Cys Ala Pro Trp Arg Asp Pro Val Ser Trp Arg Gln Gly Val Thr
            100                 105                 110

Val Ile Ala Val Cys Phe Phe Val Phe Phe Ala Leu Thr Gly Met Met
        115                 120                 125

Trp Val Gln Thr Tyr Leu Tyr Ala Pro Ser Gly Thr Leu Asp Arg Ala
    130                 135                 140

Phe Leu Arg Tyr Gly Ser Asp Pro Leu Ser Ile Tyr Ala Met Leu Ala
145                 150                 155                 160

Ala Ser Leu Leu Ile Ser Pro Gly Pro Leu Leu Glu Glu Leu Gly Trp
                165                 170                 175

Arg Gly Phe Ala Leu Pro Gln Leu Leu Lys Lys Phe Asp Pro Leu Thr
            180                 185                 190

Ala Ala Val Ile Leu Gly Thr Met Trp Trp Ala Trp His Leu Pro Arg
        195                 200                 205

Asp Leu Pro Ala Met Phe Ser Gly Glu Pro Gly Ala Leu Trp Gly Val
    210                 215                 220

Ile Val Lys Gln Phe Val Ile Ala Pro Gly Met Ile Ala Ser Thr Ile
225                 230                 235                 240

Ile Ala Val Phe Val Cys Asn Lys Leu Gly Gly Ser Leu Trp Gly Gly
                245                 250                 255

Leu Leu Thr His Ala Ile His Asn Glu Leu Gly Val Asn Val Met Ala
            260                 265                 270

Glu Trp Ser Pro Ala Ala Ala Gly Leu Gly Trp Arg Pro Trp Asp Phe
        275                 280                 285

Ile Glu Phe Ala Val Ala Ile Gly Leu Val Leu Ile Cys Gly Arg Ser
    290                 295                 300

Leu Gly Ala Ala Ser Pro Asp Asn Ala Arg Leu Ala Trp Gly Asn Val
305                 310                 315                 320

Pro Pro Lys Leu Pro Gly Gly Ala Thr Asp Lys Ser Gly Ala Asn Ala
                325                 330                 335
```